US008815579B2

(12) United States Patent
Yamasaki et al.

(10) Patent No.: US 8,815,579 B2
(45) Date of Patent: Aug. 26, 2014

(54) CULTURE APPARATUS PROVIDED WITH HEAT PIPE

(71) Applicant: Panasonic Healthcare Co., Ltd., Toon (JP)

(72) Inventors: Naoyuki Yamasaki, Gunma (JP); Yasuhiro Kikuchi, Gunma (JP); Hiroki Busujima, Gunma (JP); Yasutoshi Okamoto, Tochigi (JP)

(73) Assignee: Panasonic Healthcare Co., Ltd., Toon-shi (JP)

( * ) Notice: Subject to any disclaimer, the term of this patent is extended or adjusted under 35 U.S.C. 154(b) by 0 days.

(21) Appl. No.: 13/624,716

(22) Filed: Sep. 21, 2012

(65) Prior Publication Data

US 2013/0078714 A1      Mar. 28, 2013

(30) Foreign Application Priority Data

Sep. 22, 2011 (JP) ................. 2011-207836

(51) Int. Cl.
| | | |
|---|---|---|
| *C12M 1/00* | (2006.01) | |
| *C12M 3/00* | (2006.01) | |
| *C12M 1/02* | (2006.01) | |
| *B01L 1/00* | (2006.01) | |

(52) U.S. Cl.
CPC .............. *C12M 41/24* (2013.01); *C12N 41/12* (2013.01); *C12M 41/14* (2013.01); *B01L 1/00* (2013.01); *C12M 23/00* (2013.01); *C12M 23/02* (2013.01); *C12M 23/40* (2013.01)
USPC .................... 435/303.1; 435/283.1; 435/289.1

(58) Field of Classification Search
CPC .......... C12M 1/00; C12M 3/00; C12M 41/14; C12M 23/48; B01L 7/52; B01L 7/00; B01L 2300/0829
USPC ................. 435/283.1, 289.1, 303.1
See application file for complete search history.

(56) References Cited

U.S. PATENT DOCUMENTS

| 5,773,287 A * | 6/1998 | Binder ....................... 435/303.1 |
| 2005/0084420 A1* | 4/2005 | Osawa et al. ............... 435/303.1 |
| 2005/0084956 A1 | 4/2005 | Tamaoki et al. |

FOREIGN PATENT DOCUMENTS

JP        05-227942 A        9/1993

OTHER PUBLICATIONS

European Search Report, mailed Nov. 26, 2012, for EP Application No. 12 18 5470, 6 pages.

* cited by examiner

*Primary Examiner* — Michael Hobbs
*Assistant Examiner* — Timothy Barlow
(74) *Attorney, Agent, or Firm* — Seed IP Law Group PLLC

(57) ABSTRACT

A culture apparatus includes a heat insulating box main body having an inner box; a culture vessel; a duct and a circulation blower forcing convection of a gas in the culture vessel; a humidifying pan disposed on the bottom of the culture vessel and positioned inside the duct; a heat pipe having a heat insulating section, a heat input section disposed at one end of the heat insulating section and a heat dissipation section disposed at the other end of the heat insulating section. The heat pipe is attached to the culture apparatus with the heat dissipation section being disposed outside the culture apparatus, the heat insulating section passing through the heat insulating box main body and the inner box, and the heat input section being disposed in a gas passage in the duct.

20 Claims, 2 Drawing Sheets

CULTURE APPARATUS PROVIDED WITH HEAT PIPE

BACKGROUND OF THE INVENTION

1. Field of the Invention

The present invention relates to a culture apparatus provided with a heat pipe.

2. Description of the Related Art

A culture apparatus is used to grow a culture such as cells or microorganisms in a culture vessel. Such a culture apparatus is provided with a heater for heating the inside of the culture vessel having a humidifying pan placed therein. For example, the culture apparatus is designed such that the heater is controlled to maintain the temperature inside the culture vessel at a prescribed temperature (for example, 37° C.) and to maintain the humidity inside the culture vessel at a prescribed humidity (for example, 95% RH) suitable for the prescribed temperature.

For example, a culture apparatus disclosed in Patent Literature 1 includes a bottom heater for heating water in a humidifying pan, a heater for heating the inside of a culture vessel other than the humidifying pan, and a heater attached to a heat insulating door openably attached to a heat insulating box main body. These three heaters are controlled independently to maintain the temperature of water in the humidifying pan lower than the temperature inside the culture vessel so that supersaturated water in the culture vessel returns to the humidifying pan to thereby suppress dew condensation. This culture apparatus includes a temperature sensor for detecting the temperature inside the culture vessel and a temperature sensor for detecting outside air temperature. The above three heaters are controlled independently according to the results of detection by the two temperature sensors.

CITATION LIST

Patent Literature

[Patent Literature 1] Japanese Patent Application Laid-Open No. Hei. 5-227942

Generally, the function of a heater is not cooling but heating. Therefore, to maintain the prescribed relation between the temperature of water in the humidifying pan and the temperature inside the culture vessel by controlling these temperatures by using only heaters as described for the culture apparatus disclosed in Patent Literature 1, the temperature sensors are required to have, for example, appropriate detection accuracy. The prescribed relation between the two temperatures means that the temperature of water in the humidifying pan is lower than the temperature inside the culture vessel to the extent that the humidity inside the culture vessel can be maintained at a humidity close to a saturated water vapor density while the occurrence of dew condensation at positions where the culture in the culture vessel may be affected is suppressed. However, one problem that must be solved to achieve the prescribed relation is that dew condensation occurs around the humidifying pan because the temperature of the humidifying pan becomes low.

When such dew condensation occurs, unwanted bacteria occur in the condensed water, causing a problem in that the culture is adversely affected.

SUMMARY OF THE INVENTION

It is an object of the present invention to solve the conventional problems to provide an economical culture apparatus that can suppress adverse effects on a culture by preventing dew condensation and can be produced at low cost.

To solve the conventional problems, the inventor has made extensive studies. The inventor has found that the conventional problems can be solved by a culture apparatus configured as follows and thus arrived at the invention. A heat pipe having a heat input section and a heat dissipation section is attached to a prescribed position of the culture apparatus. The heat pipe is designed such that, when the humidity inside the culture vessel approaches, for example, a saturated water vapor density, dew condensation occurs on the heat input section and a heat insulating section in proximity thereto and the condensed water is allowed to flow downward and enter the humidifying pan so that the stored water can be used repeatedly as humidifying water.

To achieve the above object, a first aspect of the invention provides a culture apparatus including: a heat insulating box main body having an opening on a front side thereof; a heat insulating door openably attached to the heat insulating box main body; a transparent inner door that seals the opening in an openable-closable manner; a culture vessel for culturing cells or microorganisms, the culture vessel being surrounded by the inner door and the heat insulating box main body; a duct and a circulation blower that are used to cause forced convection of a gas such as air in the culture vessel; and a humidifying pan disposed on a bottom of the culture vessel and positioned inside the duct, the humidifying pan being configured to store humidifying water used to control humidity inside the culture vessel, wherein the heat insulating box main body includes an outer box made of a metal, an inner box made of a metal, a heat insulator disposed between the outer box and the inner box and on an inner side of the outer box, and an air layer disposed on an inner side of the heat insulator, wherein the culture apparatus further includes a heat pipe having a heat insulating section, a heat input section disposed at one end of the heat insulating section, and a heat dissipation section disposed at the other end of the heat insulating section, the heat pipe being attached to the culture apparatus with the heat dissipation section being disposed outside the culture apparatus, the heat insulating section being disposed passing through the heat insulating box main body and the inner box, and the heat input section being disposed in a gas passage in the duct, so that water condensed on the heat input section and the heat insulating section in proximity thereto flows downward and enters the humidifying pan and can be repeatedly used as the humidifying water.

In a second aspect of the invention, the culture apparatus of the first aspect is configured such that the heat insulating section reaching the gas passage in the duct is bent downward at a bending portion such that a portion of the heat pipe that extends from the bending portion to the heat input section is parallel to a corresponding part of the duct.

In a third aspect of the invention, the culture apparatus of the first or second aspect further includes a heat insulating sealing member interposed between the inner box and a portion of the heat insulating section that passes through the inner box.

Advantageous Effects of the Invention

The culture apparatus according to the first aspect of the invention includes: a heat insulating box main body having an opening on a front side thereof; a heat insulating door openably attached to the heat insulating box main body; a transparent inner door that seals the opening in an openable-closable manner; a culture vessel for culturing cells or microorganisms, the culture vessel being surrounded by the inner door and the heat insulating box main body; a duct and a circulation blower that are used to cause forced convection of a gas such as air in the culture vessel; and a humidifying pan disposed on a bottom of the culture vessel and positioned inside the duct, the humidifying pan being configured to store humidifying water used to control humidity inside the culture vessel, wherein the heat insulating box main body includes an outer box made of a metal, an inner box made of a metal, a heat insulator disposed between the outer box and the inner box and on an inner side of the outer box, and an air layer disposed on an inner side of the heat insulator.

The culture apparatus further includes a heat pipe having a heat insulating section, a heat input section disposed at one end of the heat insulating section, and a heat dissipation section disposed at the other end of the heat insulating section, the heat pipe being attached to the culture apparatus with the heat dissipation section being disposed outside the culture apparatus, the heat insulating section being disposed passing through the heat insulating box main body and the inner box, and the heat input section being disposed in a gas passage in the duct, so that water condensed on the heat input section and the heat insulating section in proximity thereto flows downward and enters the humidifying pan and can be repeatedly used as the humidifying water.

This culture apparatus is configured such that the heat pipe having the heat input section and the heat dissipation section is attached to a prescribed position of the culture apparatus, and when the humidity inside the culture vessel approaches a saturated water vapor density, dew condensation occurs on the heat input section, and the condensed water flows downward, enters the humidifying pan, and can be repeatedly used as the humidifying water. Therefore, the culture apparatus provided has the following advantageous effects: dew condensation is prevented, and adverse effects on the culture are thereby suppressed; the culture apparatus can be operated with the circulation blower in the duct being operated so that unevenness in temperature and humidity inside the culture vessel is prevented; and the culture apparatus can be produced at low cost and is economic.

In the second aspect of the invention, the culture apparatus according to the first aspect is configured such that the heat insulating section reaching the gas passage in the duct is bent downward at a bending portion such that a portion of the heat pipe that extends from the bending portion to the heat input section is parallel to a corresponding part of the duct.

Therefore, this culture apparatus has a further advantageous effect in that dew condensation occurs on the portion of the heat pipe that extends from the bending portion to the heat input section and the condensed water flows downward by gravity and enters the humidifying pan without being splattered.

In the third aspect of the invention, the culture apparatus of the first or second aspect further includes a heat insulating sealing member interposed between the inner box and a portion of the heat insulating section that passes through the inner box. Therefore, this culture apparatus has a further advantageous effect in that, since the heat insulating sealing member is interposed between the inner box and the heat insulating section of the heat pipe, the gas flowing through the gas passage is prevented from leaking, so that the culture vessel is not adversely affected and dew condensation is prevented from occurring on the contact portion between the heat insulating section and the inner box.

DETAILED DESCRIPTION OF THE PREFERRED EMBODIMENT

An embodiment of the invention will next be described with reference to the drawings.

Figure 1:
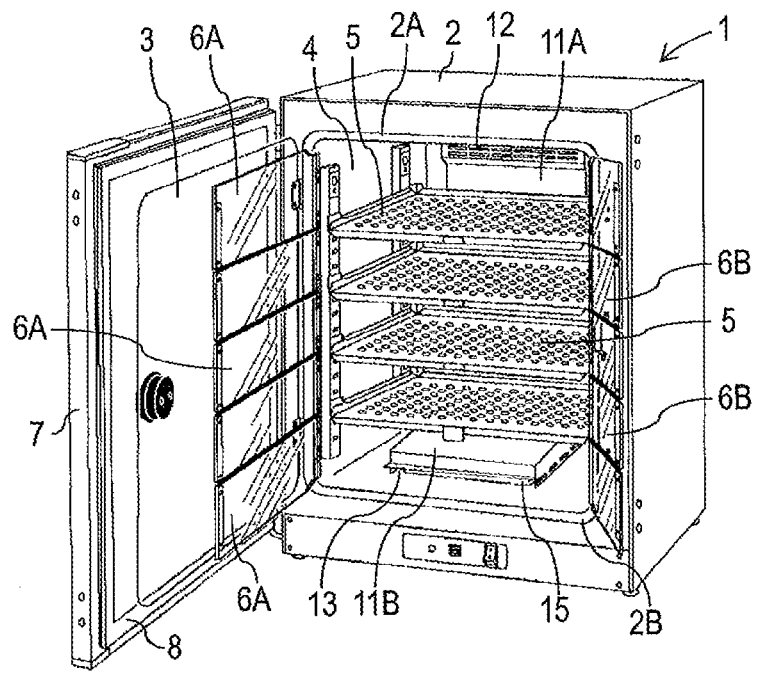
FIG. 1 is a perspective view illustrating an culture apparatus of the present invention provided with a heat pipe when a heat insulating door of the culture apparatus is opened.
Figure 2:
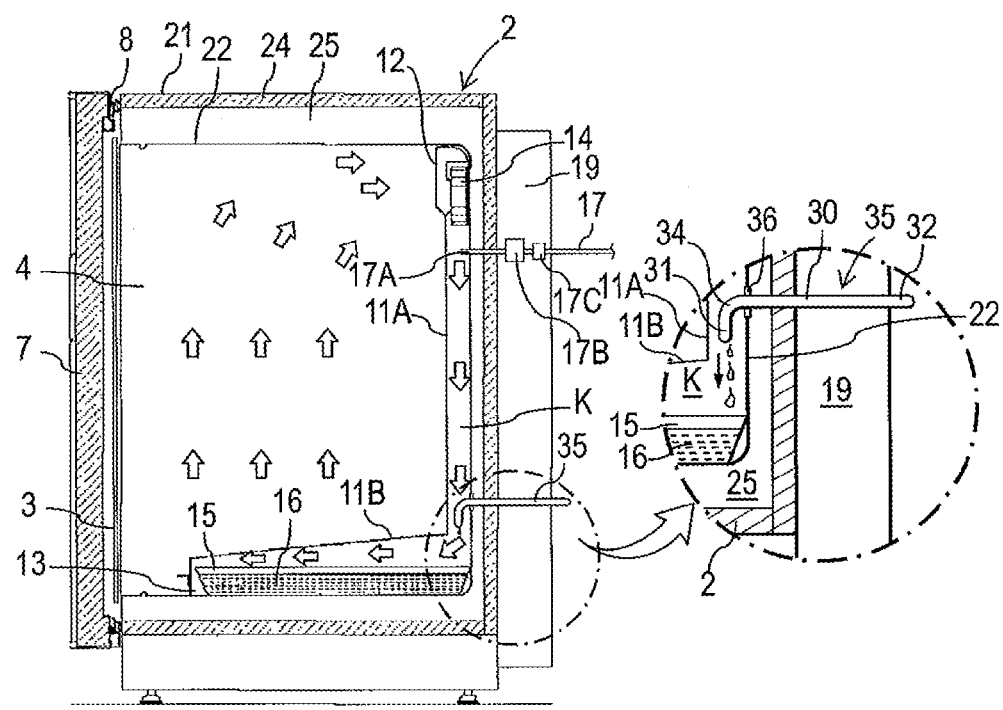
FIG. 2 is a cross-sectional view illustrating the culture apparatus as viewed from the right side, describing circulation of air mainly in a culture vessel and a duct in the culture apparatus provided with the heat pipe of the present invention.

A culture apparatus 1 in the embodiment of the present invention includes doors that open from the right (more specifically, an outer door and an inner door) and small double doors as shown in FIGS. 1 and 2. A culture vessel 4 is formed as a space surrounded by a heat insulating box main body 2 having an opening 2A on its front side and a transparent door 3 used as an inner door that can seal the opening 2A in an openable-closable manner. The left side of the transparent door 3 is hinged to the heat insulating box main body 2 in an openable-closable manner, and the transparent door 3 can hermetically seal the opening 2A through a gasket 2B disposed on an opening portion of the culture vessel 4. The sealing member (gasket) 2B for sealing the transparent inner door 3 and the heat insulating box main body 2 is disposed on the opening of the culture vessel 4.

The inside of the culture vessel 4 is vertically partitioned by a plurality of shelves 5 (into 5 sections by 4 shelves in this embodiment). When the culture apparatus 1 is, for example, a $CO_2$ incubator, the concentration of $CO_2$ is often set to and maintained at about 5%, and $CO_2$ gas is supplied to the inside of the culture vessel 4 to control the concentration of $CO_2$ after the doors are closed. Therefore, a plurality of pairs of small double doors 6A and 6B for the plurality of partitioned sections (5 pairs in this embodiment) are provided on the inner side of the inner door 3 so that outside air is prevented from entering the entire culture vessel 4 partitioned into the partitioned sections even when the inner door 3 is opened. Reference numeral 7 represents a heat insulating door serving as an outer door hinged to the heat insulating box main body 2 in an openable-closable manner and used to prevent heat from entering from the opening 2A of the culture vessel 4, and a gasket 8 with a magnet is provided on the rear circumference of the heat insulating door 7.

In the culture vessel 4, a duct 11 composed of a rear-side duct 11A and a bottom duct 11B is disposed on the rear side and the bottom of the culture vessel 4 so as to form a space for a gas passage K for $CO_2$ etc. A gas such as $CO_2$ in the culture vessel 4 is drawn from an inlet port 12 formed in the upper part of the rear duct 11A and is blown out into the culture vessel 4 from an outlet port 13 disposed over the front and side surfaces of the bottom duct 11B, so that the gas is forcibly circulated. A circulation blower 14 is disposed inside the duct 11 (in the upper part thereof in this embodiment) to forcibly circulate the gas such as $CO_2$. The blower 14 is composed of a fan, a motor, and a shaft. The motor is disposed in a machine room 19 (described later) on the outer rear side of the culture vessel 4, and the shaft extends from the motor in the machine room 19, passes through the rear surface of the heat insulating box main body 2, reaches the gas passage K for $CO_2$ etc., and is connected to the fan.

A humidifying pan 15 for storing humidifying water 16 (i.e., water used for humidification) is disposed on the bottom of the culture vessel 4 and positioned in the duct 11. The humidifying pan 15 is heated by a heater (not shown in any figures) disposed on the outer bottom side of an inner box 22 made of a metal (for example, stainless steel), and the water thereby evaporates. By disposing the humidifying pan 15 on the bottom of the culture vessel 4 and positioned in the duct 11, a humidified gas in the gas passage K for $CO_2$ etc. that is composed of the circulation blower 14 and the duct 11 can be more efficiently blown out into the culture vessel 4.

The motor serving as means for driving the circulation blower 14, gas supply means 17 for supplying $CO_2$ gas to the culture vessel 4, and the machine room 19 used to dispose electric components such as a control substrate (not shown) are formed on the rear side of an outer box 21 of the heat insulating box main body 2.

The gas supply means 17 includes a gas supply tube 17A, an on-off valve 17B, a filter 17C, etc., and the end portion of the gas supply tube 17A is positioned in the gas passage K.

To control the gas concentration in the culture vessel 4, the $CO_2$ gas supplied from the gas supply tube 17A can be injected into the culture vessel 4.

The heat insulating box main body 2 includes the metal-made outer box 21, the stainless steel-made inner box 22, a heat insulator 24 disposed between the outer box 21 and the inner box 22 and positioned on the inner side of the outer box 21, and an air layer (so-called air jacket) 25 disposed on the inner side of the heat insulator 24. Heaters (not shown) for heating the culture vessel are disposed on the left and right side-surfaces and top and rear surfaces of the inner box 22 forming the culture vessel 4.

In the culture apparatus 1 of the invention, a heat pipe 35 having a heat insulating section 30, a heat input section 31 disposed at one end of the heat insulating section 30, and a heat dissipation section 32 disposed at the other end of the heat insulating section 30 is attached to a prescribed position of the culture apparatus 1 as shown in FIG. 2.

The heat pipe 35 is attached such that the heat dissipation section 32 of the heat pipe 35 is disposed outside the culture apparatus 1, that the heat insulating section 30 is disposed to pass through the heat insulating box main body 2 and the inner box 22, and that the heat input section 31 is disposed in the gas passage K inside the duct 11A.

In the above configuration, water condensed on the heat input section 31 and the heat insulating section 30 in proximity thereto flows downward and enters the humidifying pan 15 and can be repeatedly used as the humidifying water 16.

The heat pipe 35 has a bent section 34 formed by bending downward the heat insulating section 30 reaching the gas passage K in the duct 11A, and a portion of the heat pipe 35 that extends from the bent section 34 to the heat input section 31 is configured to be parallel to a corresponding part of the duct 11A.

Dew condensation occurs mainly on this portion of the heat pipe 35 that extends from the bent section 34 to the heat input section 31, and the condensed water flows downward by gravity and enters the humidifying pan 15 without being splattered.

The heat insulating section 30 is disposed with a heat insulating sealing member 36 interposed between the inner box and a portion of the heat insulating section 30 that passes through the inner box 22.

Since the heat insulating sealing member 36 is interposed, the gas flowing through the gas passage K is prevented from leaking. Therefore, the culture vessel 4 is not adversely affected, and dew condensation is prevented from occurring on the contact portion between the heat insulating section 30 and the inner box 22.

Figure 3:
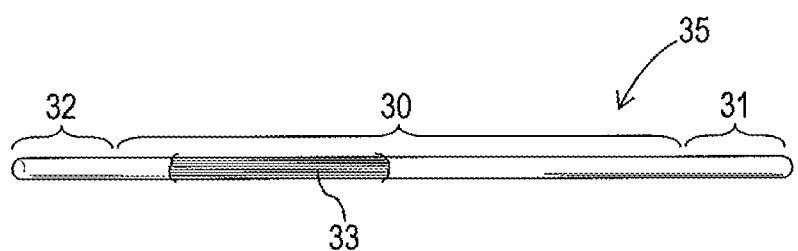
FIG. 3 is a diagram illustrating the heat pipe used in the invention.

As shown in FIG. 3, the heat pipe used in the invention includes a sealed vessel containing a small amount of liquid (operating fluid) vacuum sealed therein, and a capillarity structure (wick) 33 is provided on the inner wall of the heat pipe. The operating fluid evaporates in the heat input section 31 (absorbs the latent heat of vaporization), and the generated vapor moves toward the heat dissipation section 32. The vapor is condensed in the heat dissipation section 32 and releases the latent heat of vaporization. The condensed fluid is refluxed by capillarity in the heat input section 31. A series of phase changes occurs continuously, and the heat is thereby transferred rapidly.

In the present invention, a commercial heat pipe and a metal rod of copper, aluminum, silver, etc. can also be used.

To suppress a reduction in humidity inside the culture vessel, a heat sink for improving heat dissipation or a heater for maintaining the temperature of the heat pipe appropriately may be attached to the heat dissipation section 32 of the heat pipe.

The volume, shape, dimensions, number, etc. of the heat pipe used in the invention vary depending on the volume, shape, size, etc. of the culture apparatus and the culture to be grown.

The above described embodiment of the invention is for illustrative purposes only and is not intended to limit the claims and to reduce the scope of the invention. The configuration of each component is not limited to that in the above embodiment and can be modified variously within the technical scope described in the claims.

In the culture apparatus of the invention, the heat pipe having the heat input section and the heat dissipation section is attached to a prescribed position. When the humidity inside the culture vessel approaches, for example, a saturated water vapor density, dew condensation occurs on the heat input section, and the condensed water flows downward, enters the humidifying pan, and can be repeatedly used as humidifying water. Therefore, the culture apparatus provided has the following advantageous effects: dew condensation is prevented, and adverse effects on the culture are thereby suppressed; the culture apparatus can be operated with the circulation blower in the duct being operated so that unevenness in temperature and humidity inside the culture vessel is prevented; and the culture apparatus can be produced at low cost and is economic. Therefore, the industrial applicability of the culture apparatus is significantly high.

What is claimed is:

1. A culture apparatus comprising:
  a heat insulating box main body having an opening on a front side thereof;
  a heat insulating door openably attached to the heat insulating box main body;
  a transparent inner door that seals the opening in an openable-closable manner;
  a culture vessel for culturing cells or microorganisms, the culture vessel being surrounded by the inner door and the heat insulating box main body;
  a duct and a circulation blower that are used to cause forced convection of a gas such as air in the culture vessel; and
  a humidifying pan disposed on a bottom of the culture vessel and positioned inside the duct, the humidifying pan being configured to store humidifying water used to control humidity inside the culture vessel, wherein
  the heat insulating box main body includes an outer box made of a metal, an inner box made of a metal, a heat insulator disposed between the outer box and the inner box and on an inner side of the outer box, and an air layer disposed on an inner side of the heat insulator, and wherein the culture apparatus further comprises a heat pipe having a heat insulating section, a heat input section disposed at one end of the heat insulating section, and a heat dissipation section disposed at the other end of the heat insulating section, the heat pipe comprising a metal rod or a sealed vessel, the heat pipe being attached to the culture apparatus with the heat dissipation section being disposed outside the culture apparatus, the heat insulating section passing through a rear wall of the heat insulating box main body and the inner box and the heat input section being disposed in a gas passage in the duct, a distal end of said heat input section positioned below the heat insulating section, so that water condensed on the heat input section and the heat insulating section in proximity thereto flows downward and enters the humidifying pan and can be repeatedly used as the humidifying water.

2. The culture apparatus according to claim 1, wherein the heat insulating section reaching the gas passage in the duct is bent downward at a bending portion such that a portion of the heat pipe that extends from the bending portion to the heat input section is parallel to a corresponding part of the duct.

3. The culture apparatus according to claim 1, further comprising a heat insulating sealing member interposed between the inner box and a portion of the heat insulating section that passes through the inner box.

4. The culture apparatus according to claim 2, further comprising a heat insulating sealing member interposed between the inner box and a portion of the heat insulating section that passes through the inner box.

5. The culture apparatus according to claim 1, wherein the heat pipe is a metal rod.

6. The culture apparatus according to claim 5, wherein the metal rod is made of copper, aluminum or silver.

7. The culture apparatus according to claim 1, further comprising: a heat sink attached to the heat dissipation section.

8. The culture apparatus according to claim 1, further comprising: a heater attached to the heat dissipation section.

9. The culture apparatus according to claim 5, further comprising: a heat sink attached to the heat dissipation section.

10. The culture apparatus according to claim 5, further comprising: a heater attached to the heat dissipation section.

11. A culture apparatus comprising:
a heat insulating box including an opening on a front side thereof and providing a culture vessel for culturing cells or microorganisms therein;
a heat insulating door openably attached to the heat insulating box;
a rear duct disposed on a rear side of an inside of the heat insulating box so as to form a gas passage between the rear duct and a rear wall of the heat insulating box;
a circulation blower disposed in the rear duct to circulate a gas in the culture vessel such that the circulation blower sucks the gas in the culture vessel from one end of the gas passage and discharges from the other end of the gas passage;
a humidifying pan disposed on a bottom of the culture vessel, a part of the humidifying pan positioned below the rear duct, the humidifying pan being configured to store water for controlling humidity inside the culture vessel, and
a heat pipe including a heat insulating section, a heat input section disposed at one end of the heat insulating section, and a heat dissipation section disposed at the other end of the heat insulating section, the heat pipe comprising a metal rod or a sealed vessel, the heat insulating section passing through a side wall or a rear wall of the heat insulating box, and the heat input section disposed in a gas passage in the duct, a distal end of the heat input section positioned below the heat insulating section,
whereby water condensed on the heat input section flows downwardly along the heat input section and the water drops from the distal end of the heat input section into the inside of the humidifying pan.

12. The culture apparatus according to claim 11, wherein the heat input section is substantially parallel to the duct.

13. The culture apparatus according to claim 11, further comprising a heat insulating sealing member interposed between the heat insulating box and the heat insulating section.

14. The culture apparatus according to claim 12, further comprising a heat insulating sealing member interposed between the heat insulating box and the heat insulating section.

15. The culture apparatus according to claim 11, wherein the heat pipe is a metal rod.

16. The culture apparatus according to claim 15, wherein the metal rod is made of copper, aluminum or silver.

17. The culture apparatus according to claim 11, further comprising: a heat sink attached to the heat dissipation section.

18. The culture apparatus according to claim 11, further comprising: a heater attached to the heat dissipation section.

19. The culture apparatus according to claim 15, further comprising: a heat sink attached to the heat dissipation section.

20. The culture apparatus according to claim 15, further comprising: a heater attached to the heat dissipation section.

* * * * *